United States Patent [19]

Ryan

[11] 4,171,353

[45] Oct. 16, 1979

[54] IMMUNIZATION OF ANIMALS USING CHOLINE ESTERS AS AN IMMUNOLOGICAL ADJUVANT

[76] Inventor: Wayne L. Ryan, 3631 S. 116th Ave., Omaha, Nebr. 68144

[21] Appl. No.: 906,626

[22] Filed: May 16, 1978

[51] Int. Cl.$^2$ .................... A61K 39/00; A61K 39/02; A61K 39/12

[52] U.S. Cl. .................................... 424/88; 424/89; 424/92; 424/300; 424/311; 424/329

[58] Field of Search .................... 424/329, 88, 89, 92, 424/300, 311

[56] References Cited

PUBLICATIONS

Herlyn et al.-Chem. Abst., vol. 85, (1976), p. 3759v.

Ignat'ev et al.-Chem. Abst., vol. 76, (1972), p. 122,364m.

*Primary Examiner*—Sam Rosen

*Attorney, Agent, or Firm*—Larson, Taylor and Hinds

[57] ABSTRACT

An enhanced immune response is obtained in the immunization of animals with antigens by administrating with said antigens as an immunological adjuvant, a choline ester having the structure:

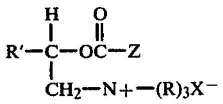

wherein R is lower alkyl, R' is selected from H and R, Z is selected from $NH_2$ and R and X is halo.

29 Claims, No Drawings

IMMUNIZATION OF ANIMALS USING CHOLINE ESTERS AS AN IMMUNOLOGICAL ADJUVANT

FIELD OF THE INVENTION

This invention relates to improvements in the immunization of animals and to novel compositions for use in such immunizations.

BRIEF DESCRIPTION OF THE PRIOR ART

Oral immunization against diseases caused by certain bacteria, viruses and other antigens has previously been demonstrated by the studies of many experts in this field. In addition, considerable time and money has been spent in an effort to discover more effective immunological adjuvants for the antigens employed in these oral immunizations. Efforts in immunization have focused principally on three areas: (1) adjuvants that provide long lasting prophylactic immunization so as to employ a minimum number of dosages, (2) adjuvants for use in the preparation of antibodies for therapeutic antisera and for use in diagnostic reagents and (3) adjuvants which will enhance the immune response in man to protect him against diseases which produce a low level of immunity such as tuberculosis.

The immunological adjuvants most commonly used to enhance immune responses in animals including man, are generally referred to as "repository adjuvants." These are of two basic types: (1) the complexing type adjuvants and (2) the oil-in-water emulsion type adjuvants. Illustrative of the complexing type adjuvants are aluminum phosphate, aluminum hydroxide, calcium phosphate and similar compounds which precipitate and complex with the antigen so as to insolubilize it. By virtue of this insolubilization, the antigen is thereafter released more slowly from the site of the injection. The oil-in-water emulsion type adjuvants on the other hand, similarly provide a slow release of the antigen by virtue of its emulsified state in the oil. Of these two basic types of adjuvants the water-in-oil type produces much higher titers of antibodies but it is more likely to produce nodules and abscesses at the site of the injection. Consequently, the water-in-oil emulsion types of adjuvants are rarely used in the immunization of humans.

The immunological adjuvants known to those skilled in the art number in the hundreds and most all of them fall into the categories described by the World Health Organization, that is, they act as repository agents, induce inflammation and stimulate lymphoreticular tissue. Unfortunately, the immune response elicited by most of the known adjuvants leaves much to be desired. In addition, it has not heretofore been possible to administer the antigens with any of the known adjuvants orally and obtain both an oral and systemic immunity. Either parenteral administration is required and/or both oral and systemic immunity are usually not obtained.

Oral immunization to any antigen is usually difficult to achieve. The difficulty may arise from getting the antigen in an unaltered form to the active lymphocytic tissue in the intestine. However, it is more likely that the difficulty stems from the tendency of oral immunization to result in immunological inhibition rather than stimulation. The inhibition of the immune response by oral feeding of protein antigens has been known since 1911 when Wells and Blume found that guinea pigs fed corn develop immunological tolerance (immunological unresponsiveness) to corn proteins. (J. Infect. Diseases 8, 66–124, 1911.) More recently, this problem was examined by Hanson, D.G., et al., who describes a profound state of specific immunological unresponsiveness following ingestion of a protein. This phenomenon suggests why it has been so difficult to produce a good immunological response by oral administration of antigen. Thus, heretofore the usual response to an antigen generally is immunological tolerance (International Archs. Allergy Applied Immun. 55, 526, 1977.)

Yet another shortcoming of the known adjuvants resides in their failure to achieve tumor immunization by oral administration thereof with tumor cells.

Needless to say, in spite of the vast number of immunological adjuvants known today, a demand continues to exist for more effective adjuvants.

OBJECTS OF THE INVENTION

Accordingly, it is an object of the invention to enhance the immune response obtained in the immunization of animals by administering to the animals as an immunological adjuvant certain parasympathomimetic agents.

It is also an object of the invention to provide a method whereby both oral and systemic immunity is obtained by oral immunization.

Yet another object of the invention is to provide novel immunological compositions and articles of manufacture useful in the immunization of animals.

Another object of the invention is to provide a method for obtaining immunity against tumors by oral administration of tumor cells.

SUMMARY OF THE INVENTION

These and other objects of the invention are obtained by employing in the immunization of animals by the administration thereto of an antigen, a choline ester as an immunological adjuvant, said choline ester having the structure:

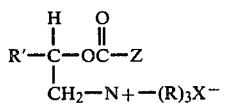

wherein R is lower alkyl, of say 1 to 4 carbon atoms; R' is selected from H and R, Z is selected from $NH_2$ and R, and X is halo, preferably chloro.

It has been surprisingly found that the choline esters, when administered to an animal with an immunizing antigen, enhance or increase the immune response of the animal to the antigen. Heretofore, this immunological adjuvant activity of these choline esters had gone unrecognized. Moreover, the finding that the choline esters of the invention are effective immunological adjuvants is particularly surprising since they possess none of the characteristics of known adjuvants. As aforementioned, all of the prior art of adjuvants act as repository agents, induce inflammation and stimulate lymphoreticular tissue. Since the choline esters of the invention are not known to induce inflammation or act as repository agents, they clearly represent a new unrecognized class of immunostimulants.

Another unique and unexpected feature which marks the present invention is the fact that use of the choline esters as immunological adjuvants enables achievement of both oral and systemic immunity by oral immunization. Thus, the present invention significantly increases protection against agents that infect the gastrontestinal tract, as for example, *Salmonella typhimurium* and toxigenic strains of *E. coli*. At the same time, the response to antigens which attack the animal systemically are also markedly increased.

DETAILED DESCRIPTION OF THE INVENTION

Thus, the novel compositions of the invention comprise an antigen capable of inducing immunization upon administration to an animal in combination with the defined choline esters as immunological adjuvants. The optimum amount of the choline esters employed in the compositions of the invention will vary depending principally upon the particular antigen and choline ester employed and the animal being immunized. In all instances, the choline ester will be present in effective concentrations, that is, concentrations that will enhance or increase the immune response beyond that normally produced by the antigen employed in combination therewith. With respect to the dose of choline ester, it has been found that the effectiveamount of choline ester generally conforms to the amount required to induce a pharmacological response such as an increased motility in the gut and increased salivation. These responses are evidence of parasympathetic stimulation. Since the amount of choline ester that induces a pharmacologic response is a function of body weight, the dosage for smaller animals will be less than that for larger animals. In man, for instance, the pharmacologic dose by mouth of bethanechol is 5–30 mg. and of methacholine is 10–100 mg. Carbachol is more stable and consequently, the pharmacologic dose by mouth in man is 0.2 to 0,8 mg. (Pharmacologic Basis of Therapeutics, Third Edition, Goodman and Gilman). In dogs the dose of choline ester is reduced about 10 fold.

What constitutes an effective amount of antigen varys widely depending especially on the agent selected. Usually a dosage of at least 0.10 mg/kg. of body weight is employed.

Antigens used in oral immunizations are highly susceptible to attack and destruction by the stomach acids and enzymes. Consequently, it is preferred to protect the antigens against such action so as to permit the entry into the small intestine. The present invention contemplates as preferred embodiments three different ways of achieving this protection:

I. Enterically coat or encapsule the composition of the invention. Any of the conventional enteric coatings or capsules of the prior art may be employed for this purpose.

II. Include in the composition of the invention a compound known to inhibit or block stomach acid and pepsin release from the stomach. Illustrative of compounds known to possess this activity are antihistamines such as cimetidine. The particular animal being immunized will generally dictate the amount necessary to effect the desired blocking action. Such amounts are either known or easily determined.

III. Include in the composition of the invention an alkaline material or buffer such as sodium bicarbonate in amounts that neutralize or reduce stomach acid.

The choline esters preferred for use according to the present invention are bethanechol chloride, i.e. (2-hydroxypropyl) trimethylammonium chloride carbamate; methacholine chloride, i.e. (2-hydroxypropyl) trimethyl ammonium chloride acetate and carbachol chloride, i.e. (2-hydroxyethyl) trimethyl ammonium chloride carbamate. Of these esters, especially preferred is bethanechol chloride.

The antigens contemplated for use in the present invention include all the antigens known in the art to induce immunization, at least to some degree, in animals when administered orally. Classes of such antigens include for instance, bacteria, viruses, tumor cells, toxins and like infectious agents. Specific examples of antigens that can be employed are as follows:

*Brucella abortus*
*E. coli*
*Pasteurella multocida*
Cholera
Shigella
Salmonella
Tumor cells The antigens can be live, killed or attenuated using any of the conventional methods and techniques reported in the literature. In most instances, it is the live viable antigens which provide the maximum immunity.

The immunological compositions of the invention can be prepared in dosage form and administered daily until adequate or complete protection is obtained. The dosage regimen will vary depending on the type of antigen used and the animal being immunized and frequently a single dose will be sufficient to induce the desired immunity.

In accordance with the method of the invention, the choline esters may be administered before or simultaneously with the administration of the antigen. While an enhanced response is obtained using either procedure it may be necessary in order to achieve adequate immunization to administer the immunological adjuvant before giving the antigen. In either case, the amount of antigen administered whether in a single or multiple dose is an effective amount, i.e. sufficient to produce some degree of protection against the infectious agent and the amount of choline ester employed will be an effective amount, i.e. that sufficient to enhance the immunity response experienced when the antigen is administered alone. Both the amount of the antigen and the amount of the choline ester vary depending primarily upon the animal, the antigen and adjuvant selected, and whether or not the immunization is being effected by single or multiple doeses.

In a preferred aspect of the method of the invention a pharmaceutically acceptable specific antagonist of cholinergic agents such as atropine is administered to the animal in addition to the choline ester and antigen. The choline esters of the present invention tend to increase the tone, amplitude of contraction and peristalsis of the gastrointestinal tract. Thus, the antigen administered may well be passed through the tract before it has had an opportunity to effect its maximum immunization activity. Specific antagonists of cholinergic agents such as atropine reduce this motility of the gastrointestinal tract. The preferred procedure when a specific antagonist of cholinergic agents is employed is to first orally administer the choline ester, wait a short period of time such as about one-half hour to one and one-half hour, orally administer the antigen and then immediately administer intraperitoneally the specific antagonist.

The following examples are included to further illustrate the invention but are not to be considered as limiting the scope thereof in any manner.

EXAMPLE I

Canine distemper virus at a titer of $1\times10^8$ is added to 2.0 mg. of bethanechol and the mixture is placed in an enteric capsule prepared as described in the Example of U.S. Pat. No. 3,826,666, hereby incorporated by reference.

EXAMPLE II

Tumors (L1210 leukemia cells in $BD2F_1$ mice) at a titer of $50\times10^6$ cells are mixed with 1.5 mg of bethanechol and the mixture is placed in an enteric capsule as in Example I.

EXAMPLE III

An immunological composition for dogs is prepared by mixing the tumor cells of Example II at a titer of $75\times10^6$ cells with 100 mg. of cimetidine and 8.0 mg. of bethanechol.

EXAMPLE IV

The tumor cells of Example II at a concentration of $0.5\times10^6$ cells are mixed with 1.0 mg of bethanechol to which is also added 25 mg of tris(hydroxymethyl) aminomethane.

EXAMPLE V

A culture of *Brucella abortus* is prepared by the procedure described in Infection and Immunity, p. 454, 5, 1972, M. Richardson and G. H. Conner. Briefly this comprises growing the organism on tryptose agar in 5% $CO_2$ for 72 hours at 37° C. The bacteria are washed from the agar with 0.85% NaCl in 0.5% phenol. The bacteria thus separated is washed again and suspended at $10^{10}$ microorganisms. The antigen thus prepared is mixed with 2 mg of bethanechol and 25 mg of tris(hydroxymethyl) aminomethane.

EXAMPLE VI

Toxigenic strains of *E. coli* are prepared using the procedure described in Example V above. A suspension of $10^{10}$ microorganisms is mixed with 2 mg. of bethanechol and 25 mg. of tris (hydroxymethyl) aminomethane.

EXAMPLE VII $BD2F_1$ mice are immunized to L 1210 leukemia by the following procedure:

The mice are fasted for 24 hours and intubated with 5 mg. bethanechol in 0.2 ml. saline. One hour later the mice are administered $30\times10^6$ 1210 tumor cells in 0.5 ml tris-saline by gavage using a 20 gauge, needle with 2.25 mm ball. Five minutes after administering the tumor cells, the mice are injected intraperitonically with 5 mg atropine.

For purposes of comparison, other $BD2F_1$ mice are given tris-saline alone, L 1210 cells alone, atropine+L 1210 cells and bethanechol+L 1210 cells as described above.

Two weeks after the treatments the mice are challenged by intraperitoneal injection of ether $1\times10^4$ or $1\times10^5$ L 1210 ascites cells. The results are summarized in the following Table I.

TABLE I

| | Challenge | | | |
|---|---|---|---|---|
| | 1 × 10^4 | | 1 × 10^5 | |
| Treatment | (a) | (b) | (a) | (b) |
| Tris-saline | 12.0 | 0/10 | 10.0 | 0/10 |
| L1210 cells | 11.6 | 2/10 | 11.2 | 1/10 |
| Atropine + L1210 cells | 11.1 | 2/10 | 10.7 | 1/10 |
| Bethanechol + L1210 cells | 17.7 | 7/10 | 14.1 | 2/10 |
| Bethanechol + L1210 cells + atropine | — | 8/8 | 24.5 | 8/10 |

(a) average life after challenge
(b) number of survivors over total mice

As can be seen from the data in Table I, the immunization of the mice by the oral administration of bethanechol and L 1210 leukemia tumor cells markedly increases the resistance of the mice to challenge. Best results are obtained when the combination of bethanechol and atropine are used.

EXAMPLE VIII

Ten C3H/He mice are orally immunized with bethanechol and 6C3HED lymphosarcoma tumor cells as described in Example VII. Another 10 C3H/He mice are given only tris-saline as a control. Both groups of mice are then challenged by subcutaneous injection $1\times10^6$ 6C3HED lymphosarcoma tumor cells. The non-immunized mice challenged died in 16 days with no survivors. In contrast, 8 of the 10 C3H/He mice orally immunized with bethanechol/atropine/6C3HED lymphosarcoma cells survived.

EXAMPLE IX

Example VII is repeated but using 3-MC fibrosarcoma tumor cells instead of the 6C3HED lymphosarcoma tumor cells. The results are as follows:

The C 3H/He mice orally immunized with the bethanechol/3-MC fibrosarcoma cells/atropine had 8/10 survivors at 60 days after $1\times10^6$ 6C3HED tumor cell challenge. The non-immunized mice when similarly challenged all died within 34 days.

EXAMPLE X

*Salmonella typhimurium* vaccine is prepared and heat-killed pursuant to the procedure described in R. Waldeman, R. Grunspan and R. Ganguly, "Oral Immunization of Mice with Killed *Salmonella typhimurium Vaccine*", Infection and Immunity, Vol. 6, pp. 58–61 (1972), hereby incorporated by reference. Fifty mice are immunized by giving them $1\times10^9$ of the killed S. typhimurium orally with a syringe to which is attached a gavage tube. In addition, another group of 50 mice is intubated with 5 mg. bethanechol in 0.2 ml saline, 5 mg. of cysteine followed by $1\times10^9$ of the S. typhimurium. One week later, infection is determined by counting the number of *S. typhimurium* in the spleen and intestine of the infected and vaccinated mice.

The results are shown in the following Table II which includes the data of Waldman et al, supra.

TABLE II

| 10[9] Organisms Were Given Once | | | | |
|---|---|---|---|---|
| TREATMENT | | | | |
| None | Streptomycin | Pertussis | $BeSO_4$ | Bethanechol |
| 62% | 45% | 57% | 68% | 0% |

The percentage is the number of mice having infected spleens and intestines divided by the number of mice challenged.

The data clearly demonstrate the superiority of bethanechol as an immunoadjuvant over prior art adjuvants in the oral immunization of mice with *S. typhimurium.*

EXAMPLE XI

Pigs are protected from transmissible gastroenteretis by orally administering to the pigs a $1\times10^7$ titer of attenuated virus of transmissible gastroenteritis in admixture with 5 mg. of bethanechol and 25 mg. of tris(-hydroxymethyl) aminomethane.

It is claimed:

1. In the immunization of animals with antigens, the improvement which comprises administering to said animals with said antigen an effective amount of a choline ester as an immunological adjuvant, said choline ester having the structure:

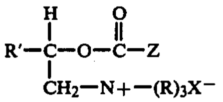

wherein R is lower alkyl, R' is selected from H or R, Z is selected from $NH_2$ or R and X is halo.

2. The improvement of claim 1 wherein R and R' are each methyl.

3. The improvement of claim 1 wherein X is chloro.

4. The improvement of claim 1 wherein Z is amino.

5. The improvement of claim 1 wherein R' is H.

6. The improvement of claim 1 wherein R' is H and R is methyl.

7. The improvement of claim 1 wherein the choline ester is (2-hydroxypropyl) trimethylammonium chloride carbamate.

8. The improvement of claim 1 wherein the choline ester is (2-hydroxyethyl) trimethylammonium chloride carbamate.

9. The improvement of claim 1 wherein Z is R.

10. The improvement of claim 1 wherein Z is R and R' is methyl.

11. The improvement of claim 1 wherein the choline ester is (2-hydroxypropyl) trimethylammonium chloride acetate.

12. The improvement of claim 1 wherein the antigen and choline ester are administered orally.

13. The improvement of claim 12 wherein the choline ester is enterically coated prior to administration.

14. The improvement of claim 12 wherein an antihistamine known to inhibit or block stomach acid and pepsin release from the stomach is administered together with the antigen.

15. The improvement of claim 13 wherein the antihistamine is cimetidine.

16. The improvement of claim 12 wherein an alkaline neutralizing agent is administered together with the antigen.

17. The improvement of claim 15 wherein the neutralizing agent is $NaHCO_3$.

18. The improvement of claim 12 wherein the choline ester is administered prior to said antigen.

19. The improvement of claim 12 wherein a specific antagonist of cholinerigic agents is administered to the animals with said choline ester and said antigen.

20. The improvement of claim 19 wherein the specific antagonist is atropine.

21. An immunological composition comprising effective amounts of an antigen capable of inducing immunization in animals when administered thereto and as an immunological adjuvant, a choline ester having the structure:

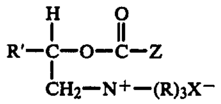

wherein R is lower alkyl, R' is selected from H or R, Z is selected from $NH_2$ or R and X is halo.

22. The immunological composition of claim 21 wherein the choline ester is (2-hydroxy propyl) trimethylammonium chloride carbamate.

23. The immunological composition of claim 21 wherein the choline ester is (2-hydroxy ethyl) trimethylammonium chloride carbamate.

24. The immunological composition of claim 21 wherein the choline ester is (2-hydroxy propyl) trimethylammonium chloride acetate.

25. The immunological composition of claim 21 including an antihistamine in amounts sufficient to inhibit or block stomach acid and pepsin release from the stomach.

26. The immunological composition of claim 25 wherein the antihistamine is cimetidine.

27. The immunological composition of claim 21 including stomach acid neutralizing amounts of an alkaline compound.

28. The immunological composition of claim 27 wherein the alkaline compound is tris(hydroxymentyl) aminomethane.

29. The immunological composition of claim 21 surrounded by an enteric coating.

* * * * *